United States Patent
Henry, Jr.

(10) Patent No.: US 12,029,616 B1
(45) Date of Patent: Jul. 9, 2024

(54) FORESKIN RESTORATION DEVICE WITH PUMP AND TWO VALVES

(71) Applicant: John Richard Henry, Jr., Mullica Hill, NJ (US)

(72) Inventor: John Richard Henry, Jr., Mullica Hill, NJ (US)

( * ) Notice: Subject to any disclaimer, the term of this patent is extended or adjusted under 35 U.S.C. 154(b) by 0 days.

(21) Appl. No.: 18/510,419

(22) Filed: Nov. 15, 2023

(51) Int. Cl.
*A61B 90/00* (2016.01)
*A61M 29/02* (2006.01)
*A61M 25/10* (2013.01)

(52) U.S. Cl.
CPC .............. *A61B 90/02* (2016.02); *A61M 29/02* (2013.01); *A61M 25/1002* (2013.01); *A61M 25/10181* (2013.11); *A61M 25/10185* (2013.11); *A61M 2210/167* (2013.01)

(58) Field of Classification Search
CPC .................. A61M 25/10181; A61M 25/10185
See application file for complete search history.

(56) References Cited

U.S. PATENT DOCUMENTS

2023/0380924 A1\* 11/2023 Losquadro ............. A61B 90/02

\* cited by examiner

*Primary Examiner* — Sameh R Boles

(57) ABSTRACT

A foreskin restoration device with a pump and two valves is disclosed for the purpose of elongating the shaft skin of the human penis to promote new skin growth. The disclosed invention comprises a gripper body comprised of an inner gripper element to hold and form an air-tight seal with the shaft skin, an outer gripper element to hold the shaft skin in position, a male annular joint element, and a first valve element that allows air to flow only into the sealed shaft skin cavity, so that the shaft skin cavity can be inflated to hold air and elongate the shaft skin. A pump body comprises a pump element, female annular joint element, and second valve element. The disclosed invention makes foreskin restoration devices more convenient and less time-consuming to operate and wear compared to other foreskin restoration devices.

2 Claims, 7 Drawing Sheets

View 1A

View 1B

Gripper body    Pump body

View 3A

View 3B

View 4A

View 4B

View 5A

View 5B

View 6A

View 6B

View 7A

View 7B

FORESKIN RESTORATION DEVICE WITH PUMP AND TWO VALVES

CROSS-REFERENCE TO RELATED APPLICATIONS

Not Applicable

BACKGROUND OF THE INVENTION

The field of the invention relates generally to foreskin restoration devices. More specifically, it relates to foreskin restoration devices that put the shaft skin of the human penis under tension by creating a seal between the rolled double layer of shaft skin and the inner gripper element of the device, wherein the outer gripper element holds the double layer of skin against the inner gripper element, wherein the shaft skin can be inflated with air so that the tension applied to the shaft skin promotes new skin growth. It is common for men in America and other countries to have had their foreskins surgically removed shortly after their birth and without their consent. This surgical practice is commonly referred to as male circumcision. A growing number of men are becoming aware of foreskin restoration through internet forums, social media sites, and other online communities. As more men become educated about the foreskin and its benefits, and as foreskin restoration continues to grow in popularity, more and more men are seeking out foreskin restoration to regain the function of their foreskin. Through foreskin restoration men can regain the look, sensation, and function of the foreskin of an intact penis. Foreskin restoration also serves as a therapeutic outlet for men that have had their foreskins surgically removed without their consent. Men often feel a sense of loss and grief when they come to recognize their bodily integrity has been infringed upon. Men who resent the nonconsensual surgical removal of their foreskin often express sense of empowerment through practicing foreskin restoration. For these men, foreskin restoration is a practical, accessible, pain free, and nonsurgical approach they can take to approximate the original function of their genital anatomy.

The practice of putting skin tissue under tension so that the skin grows over time is known as tissue expansion and has been a common practice in the field of medicine for the last 40 years. Tissue expansion as it applies to the shaft skin of the human penis is commonly referred to as foreskin restoration. Foreskin restoration is a highly personalized practice and there are number of different methods men can use to restore their foreskins. Some foreskin restoration methods work better for some men than others, and foreskin restoration device preferences are no different. Many men prefer using direct air foreskin restoration devices (DAFRDs) as their primary foreskin restoration tool, as they feel DAFRDs are the most comfortable type of device to wear, and they also feel DAFRDs create superior skin tension compared to other types of foreskin restoration devices. While air is the most widely used fluid to inflate the foreskin with DAFRDs, other fluids such as water have also been used. Other types of foreskin restoration devices use only axial tension about the penile shaft to elongate the skin. This axial tension is created by physically contacting and depressing the glans penis with material from the device. This puts pressure on the glans penis, making it uncomfortable to wear for extended timeframes. DAFRDs tensions the penis shaft skin both axially and radially about the penile shaft and DAFRDs do not directly depress the glans penis as the glans is depressed by pressurized air created in the foreskin cavity.

One of the major drawbacks of DAFRDs is that all DAFRDs that have entered the market rely on off-the-shelf inflation apparatuses that cannot be directly attached or affixed to the devices while being worn by the user, wherein the term "off-the-shelf" in the current disclosure means the inflation apparatus design is not intended for use with DAFRDs and is sourced from existing stock from an alternate manufacturer's existing design. The most common inflation apparatuses used for DAFRDs that have entered the market are off-the-shelf vinyl hosing, bulb pumps, and slip tip syringes. Using these types of inflation apparatuses is inconvenient an impractical for men that use DAFRDs for many reasons. Vinyl hosing is used to blow air via the mouth, through the device, into the foreskin cavity, but this is unsanitary as air from the mouth can introduce bacteria into the foreskin cavity. With slip tip syringes, air flow is difficult to control, and it can be physically challenging to depress the syringe plunger. Bulb pumps are larger than necessary for use with DAFRDs, are made of a hard rubber, and since the interior of bulb pumps are inaccessible they are difficult to keep clean. All of the commercially sourced inflation apparatuses mentioned in the current disclosure are bulky, difficult to operate and handle with use on DAFRDs, are time consuming to apply and to clean for daily use and are not ergonomically designed for operation with DAFRDs. Since off-the-shelf inflation apparatuses cannot remain attached to the device in any practical way while being worn by the user, this makes losing or misplacing these types of inflation apparatuses more likely.

The air control and direction into the foreskin cavity is important as there exists the chance of air entering the urethra while inflating the foreskin cavity, which occurs when the urethra opening is co-linear with the valve air stream that controls pressure in the foreskin cavity. Air entering the urethra is a concern because it is not the intended application and it can be uncomfortable and irritating to the user. To decrease the chance of air entering the urethra the user can seal the urethra with medical tape, though this is not necessary for all users. Slow and controlled air flow into the foreskin cavity reduces the chance of air entering the urethra. Additionally, the valve air flow direction can be oriented so that the valve opening does not make contact and is not co-linear with the opening of the urethra so that the air flows radially with respect to the penile shaft, thereby further decreasing the chance of air entering the urethra.

Foreskin restoration devices are most effective at generating new penis shaft skin when they are worn by the user for multiple hours per day. It is not uncommon for men to wear foreskin restoration devices for 8 to 10 hours per day. DAFRDs need to be removed to urinate, so the user must re-apply and operate the device after urination. Since the user will need to remove, re-apply, and operate the device multiple times per day there is a need for the device to be applied and operated in a reliable and time-efficient manner. Often the user's free hand is needed to maintain contact between off-the-shelf inflation apparatuses and DAFRDs, otherwise the off-the-shelf inflation apparatuses will not stay in position. This approach to inflating the foreskin is not practical for everyday use, as repositioning off-the-shelf inflation apparatuses becomes cumbersome and time consuming when done multiple times per day. As off-the-shelf inflation apparatuses cannot be affixed to DAFRDs while being worn by the user, the inflation apparatus must be carried on his person. Carrying bulky inflation apparatuses on the user's person throughout everyday activities is not practical, discrete, or time efficient and commonly leads to losing or misplacing the inflation apparatus, and without an inflation apparatus DAFRDs cannot meet the application of inflating the foreskin cavity to promote new skin growth.

BRIEF SUMMARY OF THE INVENTION

The disclosed invention is an improvement on current DAFRDs that rely on commercially sourced inflation apparatuses. The disclosed invention allows the user to create tension on the shaft skin of the user's penis to promote new skin growth without using an off-the-shelf inflation apparatus. In the disclosed invention, the pump body can remain affixed to the gripper body of the DAFRD, so that said device can be used to create tension on the shaft skin of the user's penis throughout the day to promote new skin growth. The user also has the option of removing the pump body from the gripper body and storing it on the user's person while the gripper body is being worn by the user. The disclosed invention is an improvement on existing DAFRDs as it eliminates the need for the user to carry a bulky inflation apparatus on their person and allows for quick and convenient application and operation of the device so the user can wear the device under application for multiple hours per day.

DETAILED DESCRIPTION OF THE INVENTION

The following is a detailed description of the preferred embodiment of the disclosed invention. The terminology and drawings are used to describe the disclosed invention, but the invention is not limited to the embodiments described in the current disclosure and the drawings do not limit the invention. View 1A of FIG. 1 shows a side view of an example configuration of the disclosed invention, wherein the foreskin restoration device is comprised of a gripper body 101 and a pump body 102, where the term "body" is used in the current disclosure to define a single object comprised of a uniform material which may contain one or more elements.

The gripper body 101 is comprised of a skin safe silicone rubber or similar type of flexible material. Said gripper body 101 can be manufactured using a gripper body mold, wherein said gripper body mold is comprised of a hollow cavity in the shape of said gripper body 101. A cast of said gripper body 101 can be manufactured by pouring liquid silicone rubber into a sprue on said gripper body mold and allowing the liquid silicone rubber to cure into a flexible material in the shape of the hollow cavity of the gripper body mold. Said gripper body 101 is removed from said gripper body mold and any excess sprue material is removed from said gripper body 101 with a utility knife or similar cutting tool.

The pump body 102 can be comprised of a skin safe silicone rubber or similar type of flexible material. Said pump body 102 can be manufactured using a pump body mold, wherein said pump body mold is comprised of a hollow cavity in the shape of said pump body 102. A cast of said pump body 102 can be manufactured by pouring liquid silicone rubber into a sprue on said pump body mold and allowing the liquid silicone rubber to cure into a flexible material in the shape of the hollow cavity of said pump body mold. Said pump body 102 is removed from said pump body mold and any excess sprue material is removed from said pump body 102 with a utility knife or similar cutting tool. Said gripper body mold and said pump body mold can be comprised of materials such as machined aluminum metal, molded and cured ABS plastic, or molded and cured flexible silicone rubber.

Figure 1:
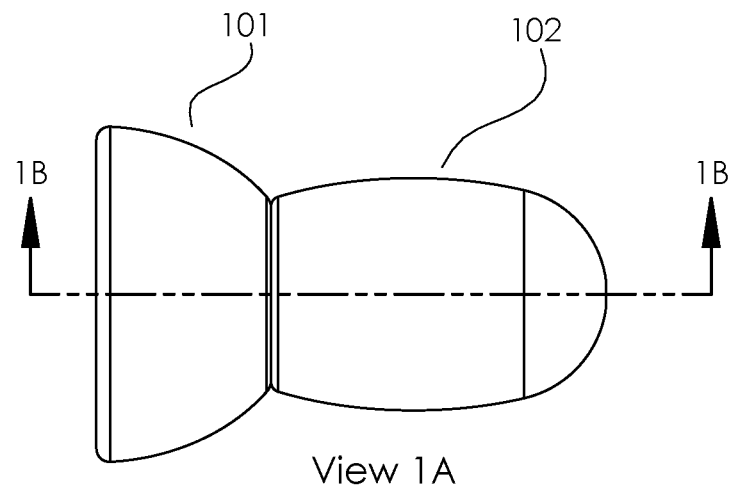
FIG. 1 shows a side view 1A and sectional view 1B of an example embodiment of the invention which is comprised of a gripper body and a pump body, wherein the outer gripper element is in a closed position and the pump element is in an uncompressed state, and a hatch legend identifying the gripper body and pump body is shown.
Figure 1:
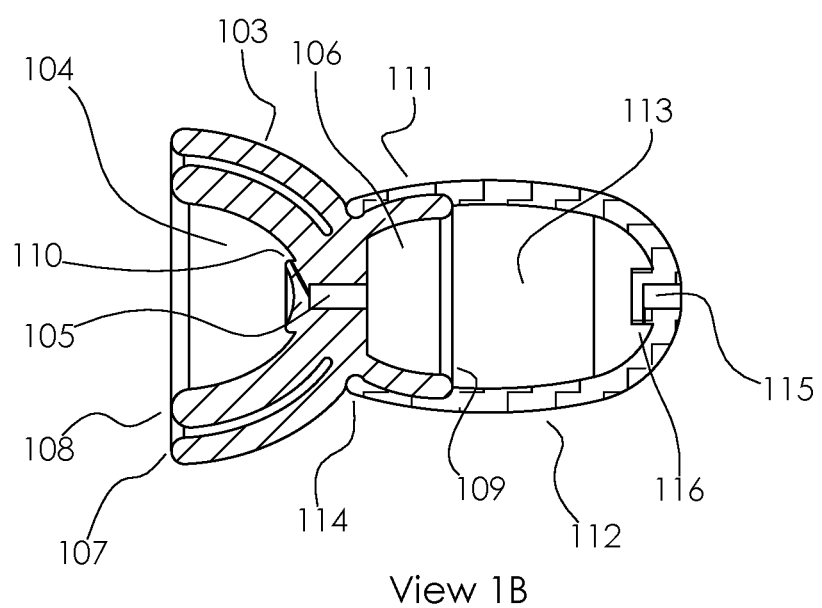
Figure 1:
Figure 1:

In View 1B of FIG. 1 the gripper body 101 is comprised of an outer gripper element 103 in a closed position, an inner gripper element 104, a first valve element 105, and a male annular joint element 106. Said outer gripper element 103 is a thin-walled shell in the shape of a truncated prolate spheroid, wherein an outer gripper truncation 107 is positioned at or near the minor co-vertex of the outer gripper prolate spheroid at the first distal end of said gripper body 101. In alternate embodiments the outer gripper element can be a thin-walled shell in the shape of a truncated cone. Said inner gripper element 104 is a thin-walled shell in the shape of a truncated prolate spheroid, wherein an inner gripper truncation 108 is positioned at or near the minor co-vertex of the inner gripper prolate spheroid at the first distal end of said gripper body 101. In alternate embodiments the inner gripper element can be a thin-walled shell in the shape of a truncated cone. The male annular joint element 106 is a thin-walled shell in the shape of a truncated prolate spheroid, wherein a male annular joint truncation 109 is located at the second distal end of the gripper body 101. The male annular joint element 106 of the gripper body 101 is inserted into a female annular joint element 111 of the pump body 102, so that said gripper body 101 and said pump body 102 are affixed. In alternate embodiments the gripper body can be comprised of a female annular joint element and the pump body can be comprised of a male annular joint element.

The major diameter of the prolate spheroid of said outer gripper element 103 is concentric with and greater than the major diameter of the prolate spheroid of said inner gripper element 104. The minor diameter of the prolate spheroid of said outer gripper element 103 is concentric with and greater than the minor diameter of the prolate spheroid of said inner gripper element 104. The first valve element 105 is a one-way valve that allows air to flow only from said male annular joint 106 towards said inner gripper truncation 108 and is positioned centrally at the major vertex of the prolate spheroid of said inner gripper element 104 and proximal to said male annular joint element 106. The first valve element 105 can be manufactured by creating a first valve incision 110 in the cured silicone with a utility knife or similar cutting tool, wherein said first valve incision 110 makes a channel from the cavity of the inner gripper element 104 to the cavity of said male annular joint element 106.

In view 1B the pump body 102 is comprised of a female annular joint element 111, a pump element 112 in the shape of a truncated prolate spheroid thin-walled shell forming a hollow pump cavity 113, wherein a pump element truncation 114 is positioned at the first distal end of said pump body 102, and a second valve element 115 is positioned at the second distal end of said pump body 102. The second valve element 115 is a one-way valve that allows ambient air to flow only into the hollow pump cavity 113 of the pump element 112 and is positioned centrally at the major vertex of the prolate spheroid of said pump element 112 at the second distal end of the pump body 102. The second valve element 115 can be manufactured by creating a second valve incision 116 in the cured silicone with a utility knife or similar cutting tool, wherein said second valve incision 116 makes a channel from the hollow pump cavity 113 to the ambient air and said second valve incision 116 is radial in direction with respect to the axis of the minor diameter of the prolate spheroid shape of said pump element 112. In alternate embodiments there can be a second valve element that is a through-hole extending from the hollow pump cavity 113 to the ambient air environment, wherein the user manually manipulates the air flow by covering the through hole valve when the pump is compressed so that air can flow only through the first valve element, and the user manually manipulates the air flow by uncovering said through hole valve so that air can flow into the hollow pump cavity 113 when the pump transitions from a compressed state to an uncompressed state.

Figure 2:
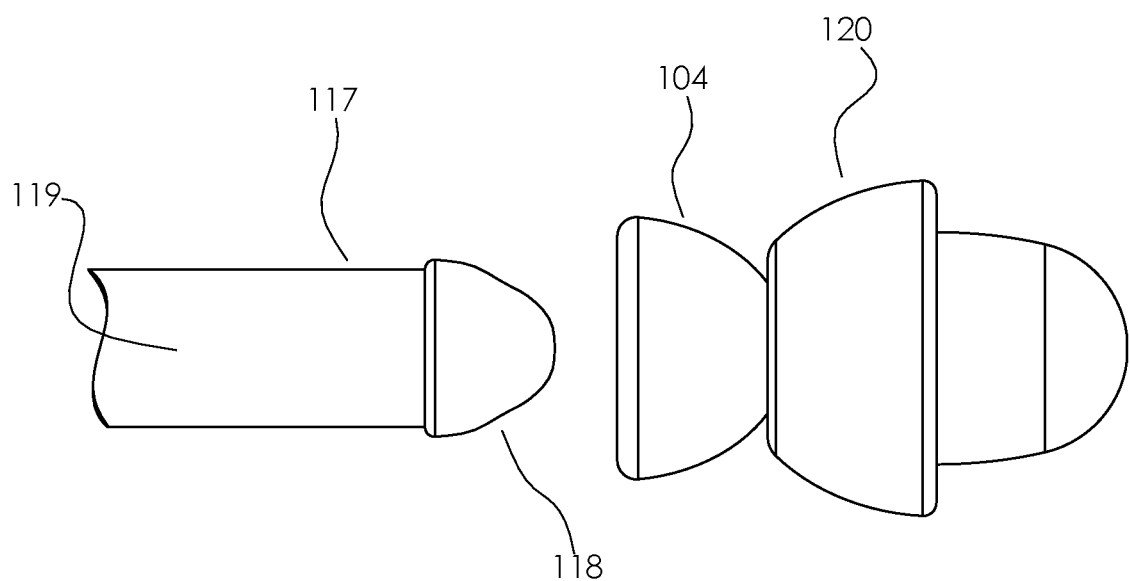
FIG. 2 shows a side view of the human penis and an example embodiment of the invention which is comprised of a gripper body and a pump body wherein the outer gripper element is in an open position and the pump element is in an uncompressed state.
Figure 3:
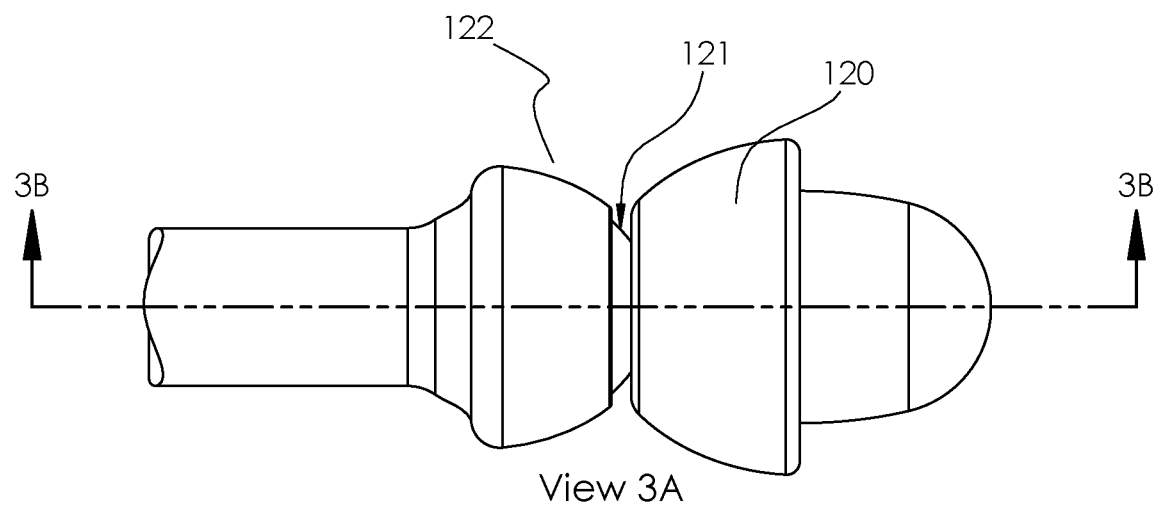
FIG. 3 shows a side view 3A and sectional view 3B of the human penis and an example embodiment of the invention which is comprised of a gripper body and a pump body, wherein the shaft skin of the human penis is rolled forward over the inner gripper element to form a double layer of skin, the outer gripper element is in an open position, and the pump element is in an uncompressed state, and a hatch legend identifying the human penis, gripper body, and pump body is shown.
Figure 3:
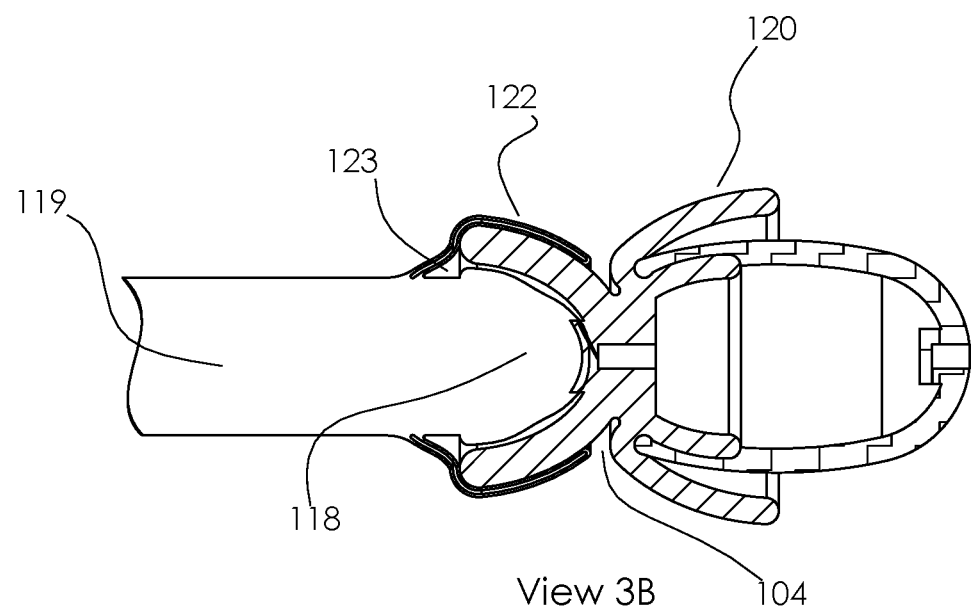

FIG. 2 shows the shaft 117 and glans 118 of the human penis 119, wherein the outer gripper element is oriented in an open position 120. In FIG. 3 view 3B the glans 118 of the human penis 119 is inserted into the interior cavity of the inner gripper element 104 with the outer gripper element in the open position 120, so that the shaft skin of the human penis can be rolled over the outer surface 121 of the inner gripper element (FIG. 3 view 3A) so that the shaft skin is folded into a double layer of skin 122, wherein an uninflated airtight shaft skin cavity 123 is created (view 3B) with the double layer of skin 122 and the inner gripper element 104.

Figure 4:
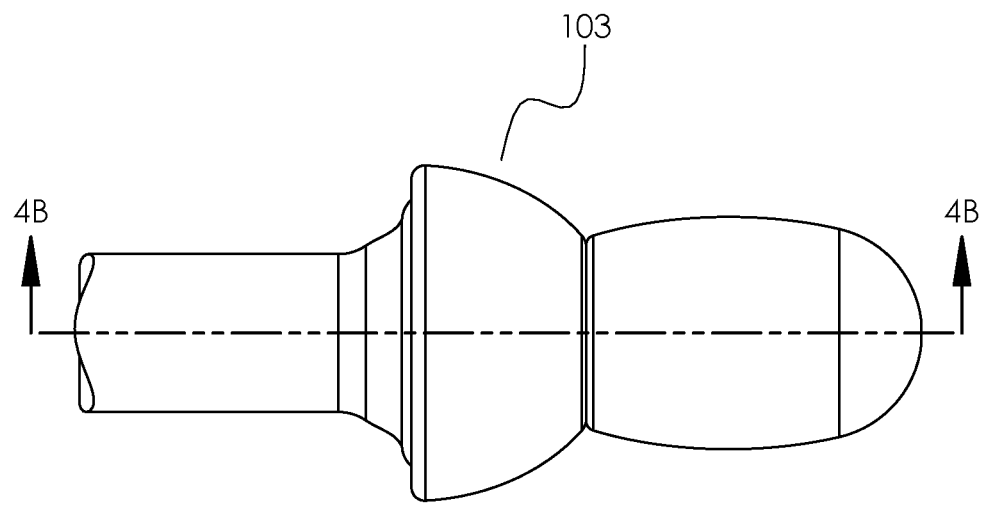
FIG. 4 shows a side view 4A and sectional view 4B of the human penis and an example embodiment of the invention which is comprised of a gripper body and a pump body, wherein the shaft skin of the human penis is rolled forward over the inner gripper element to form a double layer of skin, the outer gripper element is in a closed position, and the pump element is in an uncompressed state.
Figure 4:
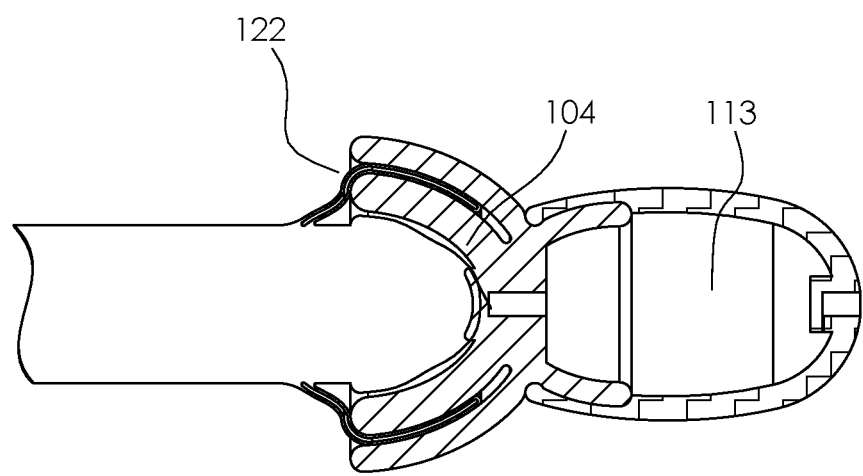
Figure 5:
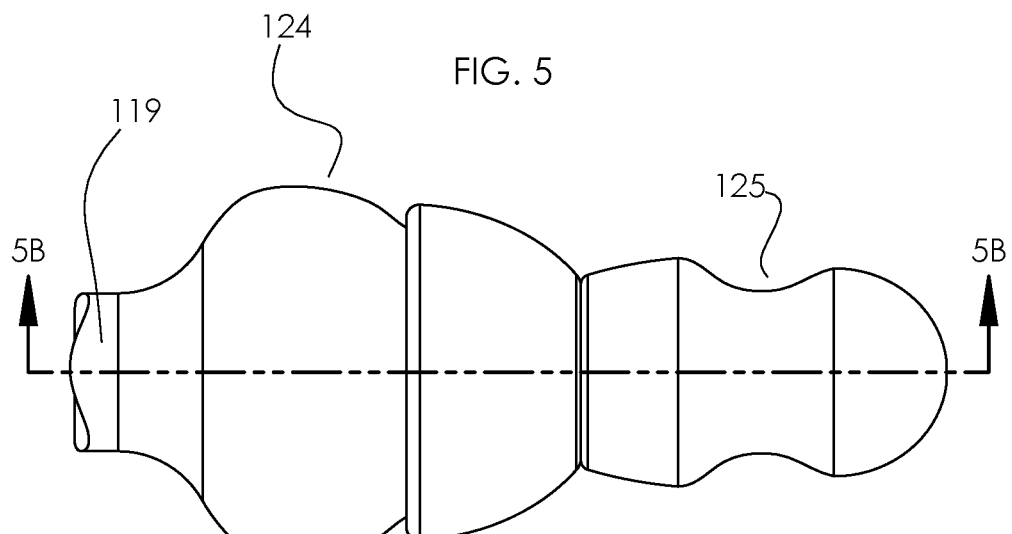
FIG. 5 shows a side view 5A and sectional view 5B of the human penis and an example embodiment of the invention which is comprised of a gripper body and a pump body, wherein the shaft skin of the human penis is rolled forward over the inner gripper element to form a double layer of skin, the outer gripper element is closed, and the pump element is in a compressed state, wherein the hollow pump cavity of the pump element is not at a maximum volume, and the shaft skin cavity is expanded under tension so that there is a cavity filled with air between the shaft skin and the inner gripper element. The air flow direction through the first valve element is illustrated with an arrow below the text "air flow direction".
Figure 5:
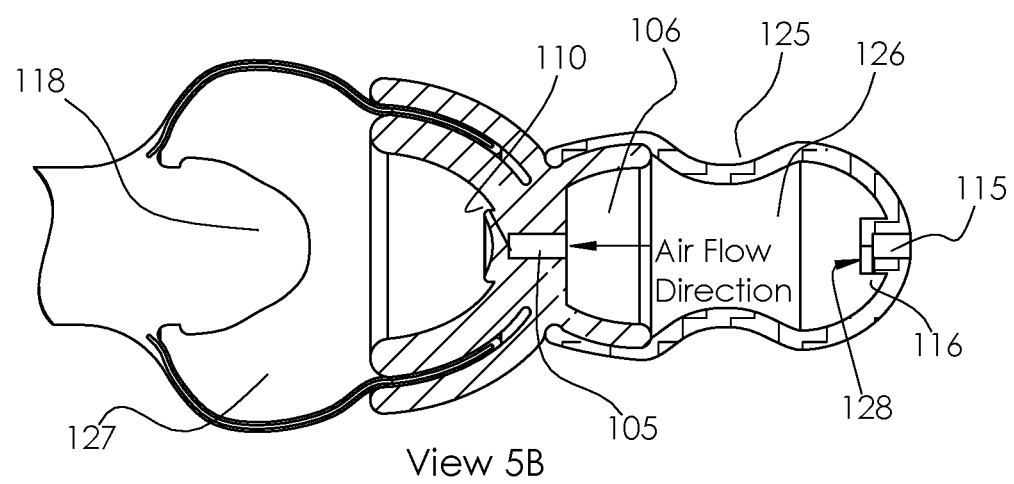

In FIG. 4 View 4A the outer gripper element 103 is shown in a closed position, wherein said outer gripper element 103 holds the double layer of skin 122 (FIG. 4 View 4B) in position. FIG. 5 View 5A shows the human penis 119, wherein the double layer of skin is expanded under tension 124, and wherein the pump element is in a compressed state 125. With the pump element in a compressed state 125 the volume of a compressed hollow pump cavity 126 (FIG. 5 view 5B) is less than the volume of the hollow pump cavity 113 (view 4B). The compressed pump element 125 (view 5B) causes the air pressure inside the compressed hollow pump cavity 126 to be greater than the air pressure in the uninflated airtight shaft skin cavity 123 (view 3B), wherein the walls of the first valve incision 110 (view 5B) expand and separate from the pressure created in the compressed hollow pump cavity 126 so that air moves from the compressed hollow pump cavity 126 into the shaft skin cavity through the first valve element 105 so that the shaft skin cavity is inflated 127 with air and the glans 118 is depressed, so that said glans 118 is pushed closer to the user's body, and the shaft skin is under tension 124 view 5A. The second valve element 115 prevents air from moving from the compressed hollow pump cavity 126 to the ambient air environment, so that the air in the compressed hollow pump cavity 126 is transferred through said first valve element 105 into the inflated shaft skin cavity 127. When the pump element is compressed 125, pressure on an inner surface 128 creates a seal with the walls of the second valve incision 116 so that the walls of said second valve incision 116 remain in contact and are not expanded so that air cannot move from the second valve element 115 to the ambient air environment.

Figure 6:
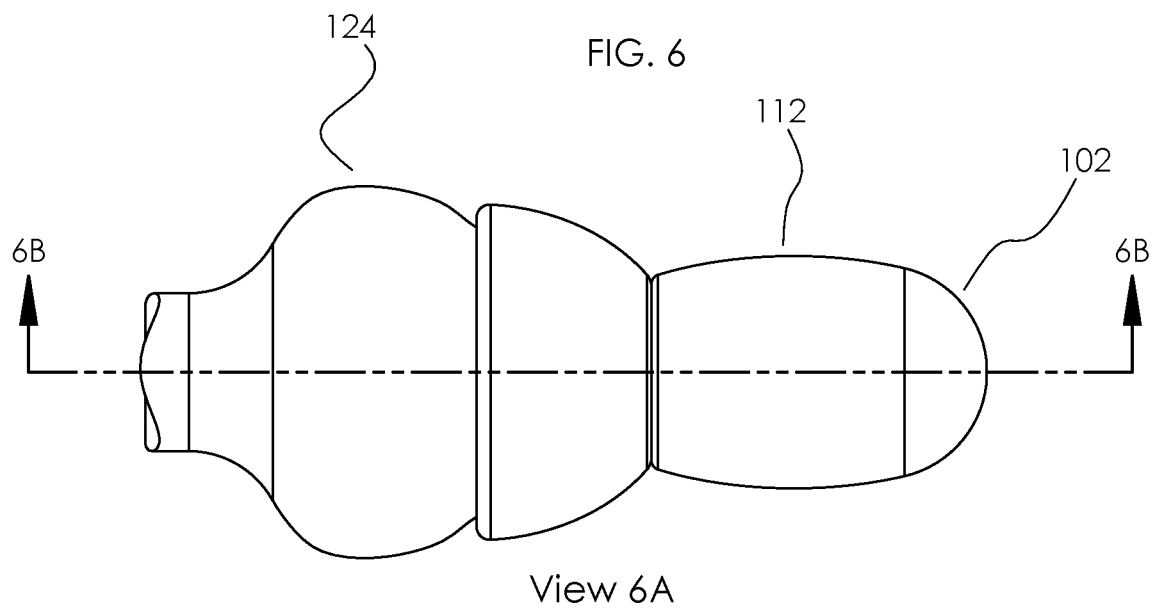
FIG. 6 shows a side view 6A and sectional view 6B of the human penis and an example embodiment of the invention which is comprised of a gripper body and a pump body, wherein the foreskin is rolled forward over the inner gripper element to form a double layer of skin, the outer gripper element is closed, the pump element is in an uncompressed state, and the shaft skin of the human penis is inflated so that there is a cavity filled with air between the shaft skin and the inner gripper element. The air flow direction through the second valve element is illustrated with an arrow below the text "air flow direction".
Figure 6:
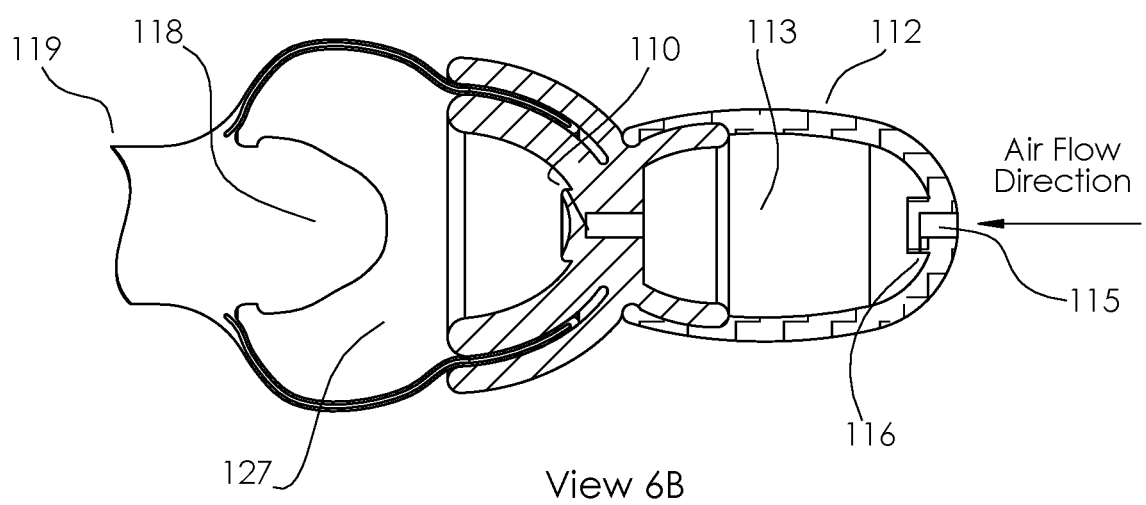

In view 6A of FIG. 6 the shaft skin is shown expanded under tension 124 from the increased pressure in the inflated shaft skin cavity 127 (FIG. 6 view 6B), wherein the pump element 112 is in an uncompressed state. When the pump element transitions from a compressed state 125 (view 5B) to an uncompressed state 112 (view 6B), the walls of the first valve incision 110 are no longer expanded and separated and air cannot escape from the inflated shaft skin cavity 127, and the pressure in the hollow pump cavity 113 is less than to the pressure in the ambient air, causing air to travel from the ambient air into the hollow pump cavity 113 through the second valve element 115 by expanding and separating the walls of the second valve incision 116 so that air can pass into the hollow pump cavity 113.

Figure 7:
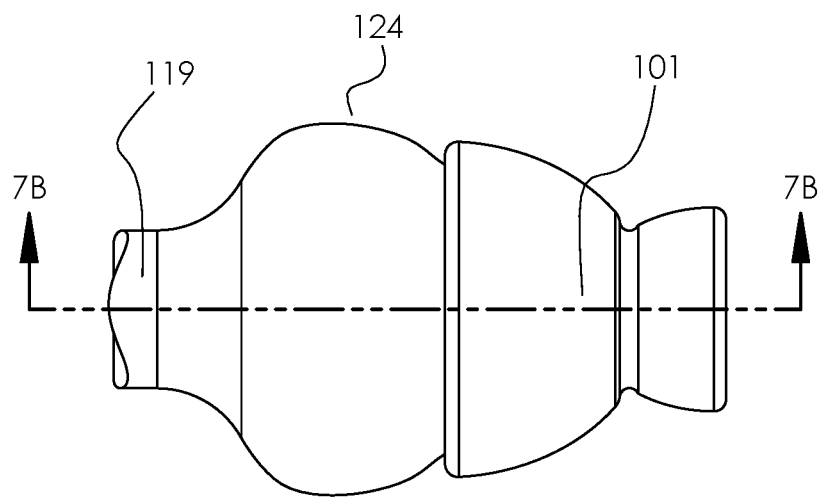
FIG. 7 shows a side view 7A and sectional view 7B of the human penis and an example embodiment of the invention which is comprised of a gripper body, wherein the pump body is not shown and not affixed to the gripper body, the shaft skin of the human penis is rolled forward over the inner gripper element to form a double layer of skin, the outer gripper element is closed, and the shaft skin is inflated so that there is a cavity filled with air between the foreskin and inner gripper element.
Figure 7:
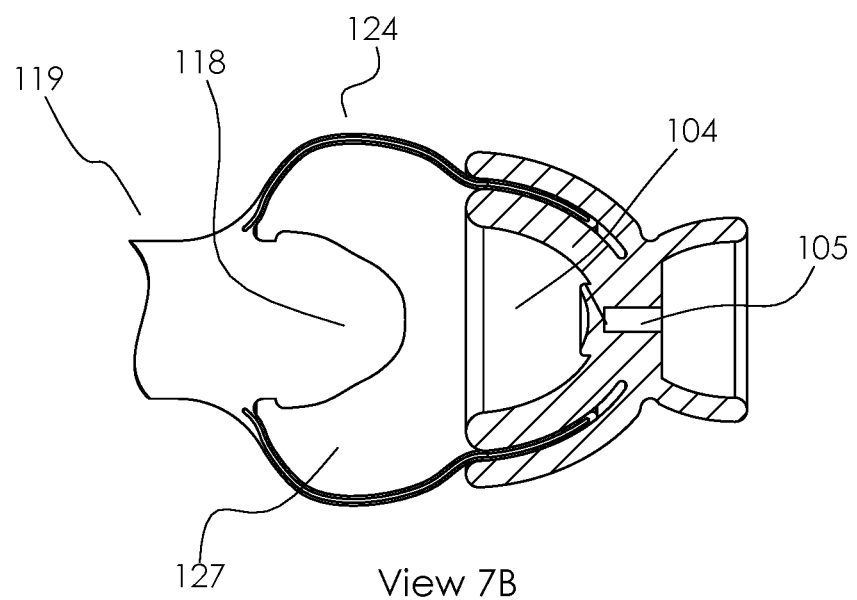

FIG. 7 view 7A shows the gripper body 101 attached to the human penis 119 wherein the pump body 102 (view 6A)

is not shown and is not affixed to the gripper body 101, with the shaft skin cavity inflated 127 (FIG. 7 view 7B) and the shaft skin under tension 124. The user has the option of leaving the pump body 102 affixed to the gripper body 101 as shown in view 6A, or of leaving said pump body 102 not affixed to said gripper body 101 as shown in view 7A. The first valve element 105 (view 7B) and the airtight seal created between the shaft skin and the inner gripper element 104 keep the shaft skin under tension 124 and the glans 118 depressed so said glans 118 is pushed closer to the user's body, and pressure is maintained in the airtight inflated shaft skin cavity 127 while the foreskin restoration device is being used in application.

What is claimed is:

1. A foreskin restoration device comprising,
A gripper body comprised of a flexible material comprising an outer gripper element in a truncated prolate spheroid thin-walled shell shape, wherein an outer gripper element truncation Is positioned at a first distal end of the gripper body; and an inner gripper element of a truncated prolate spheroid thin-walled shell shape, wherein an inner gripper element truncation is positioned at the first distal end of the gripper body, wherein said outer gripper element has a larger major and larger minor diameter than said inner gripper element and a minor diameter of said outer gripper element is positioned concentrically with a minor diameter of said inner gripper element; a first valve element centrally positioned at a major vertex of said inner gripper element, wherein said first valve element allows air to flow only in a direction toward the truncation of said inner gripper element; a male annular joint element of a truncated prolate spheroid thin-walled shell shape, wherein a truncation is located at a second distal end of said gripper body; a pump body comprised of a flexible material comprising a pump element of a truncated prolate spheroid thin-walled shell shape, wherein a truncation is positioned at a first distal end of said pump body; a female annular joint element positioned at the first distal end of said pump body, wherein said male annular joint element of said gripper body is inserted into said female annular joint element of said pump body so that said gripper body and said pump body are affixed and said pump element comprises a hollow pump cavity; and a second valve element positioned at a second distal end of said pump body, wherein air from an ambient environment can flow only into said hollow pump cavity of said pump element, wherein compression of said pump element reduces a volume of said hollow pump cavity, wherein pressure is increased in a compressed hollow pump cavity so that air flows through said first valve element in a direction of said inner gripper element, so that when compression is removed from said pump element the second valve element allows ambient air to flow into the hollow pump cavity of said pump element so that the hollow pump cavity is greater in volume than the compressed hollow pump cavity and said pump element is uncompressed and returns to the truncated prolate spheroid thin-walled shell shape.

2. The device of claim 1, wherein the pump body comprising the second valve element, wherein said second valve element comprises a through hole.

* * * * *